United States Patent [19]

Masuhara et al.

[11] 4,148,988

[45] Apr. 10, 1979

[54] CURABLE COMPOSITION

[75] Inventors: Eiichi Masuhara, Tokyo; Nobuo Nakabayashi, Matusdo; Morio Takeyama, Tokyo, all of Japan

[73] Assignee: Mitsui Petrochemical Industries Ltd., Tokyo, Japan

[21] Appl. No.: 916,851

[22] Filed: Jun. 19, 1978

[30] Foreign Application Priority Data

Jun. 28, 1977 [JP] Japan .................................. 52-76190
Oct. 13, 1977 [JP] Japan ................................ 52-121858

[51] Int. Cl.$^2$ ........................................... C08F 222/16
[52] U.S. Cl. ..................................... 526/318; 106/35; 260/901; 526/271
[58] Field of Search ......................... 260/901; 106/35; 526/MS File

[56] References Cited

U.S. PATENT DOCUMENTS

| | | | |
|---|---|---|---|
| 3,063,969 | 11/1962 | Stephens et al. ...................... | 526/272 |
| 3,223,681 | 12/1965 | Rambosek ............................... | 106/35 |
| 3,539,526 | 11/1970 | Bowen ..................................... | 106/35 |
| 3,835,090 | 9/1974 | Gander et al. .......................... | 106/35 |
| 3,932,556 | 1/1976 | Takamori et al. ...................... | 526/318 |
| 3,975,203 | 8/1976 | Dietz ....................................... | 106/35 |

*Primary Examiner*—John Kight, III
*Attorney, Agent, or Firm*—Sherman & Shalloway

[57] ABSTRACT

A curable composition comprising an aromatic dibasic acid having an ethylenically unsaturated group, such as 4-methacryloxyethyltrimellitate, or an acid anhydride thereof, other ethylenically unsaturated monomer and a catalyst is disclosed. This composition is applied between articles to be bonded together and is polymerized and cured to form an adhesive layer excellent in the water resistance and durability. This composition is especially valuable as a dental adhesive or as an undercoating agent for a paint or adhesive.

11 Claims, No Drawings

CURABLE COMPOSITION

BACKGROUND OF THE INVENTION (1) Field of the Invention

This invention relates to a curable composition comprising a specific aromatic dibasic acid having an ethylenically unsaturated group, such as 4-methacryloxyethyltrimellitate or its anhydride, an ethylenically unsaturated monomer other than said aromatic dibasic acid and a catalyst. More particularly, the invention relates to a curable composition valuable as a dental adhesive or cement or as an undercoating agent for an adhesive or paint.

(2) Description of the Prior Art

Curable compositions comprising an acrylic or methacrylic monomer such as methyl methacrylate, 2,2-bis(p-2′-hydroxy-3′-methacryloxypropoxyphenyl)propane or the like and a free-radical initiator have been proposed and used as dental adhesives or cements.

These conventional compositions, however, are still insufficient in the bonding force to enamel of teeth. Accordingly, when teeth are treated with these compositions, it is necessary to treat enamel of the teeth in advance with a strong acid and then conduct the bonding operation. Therefore, the tooth treatment becomes troublesome and enamel on the surface of a tooth is worn away by the acid treatment. It has been desired to eliminate these disadvantages involved in the conventional compositions.

BRIEF SUMMARY OF THE INVENTION

We found that when a curable composition comprising a specific aromatic dibasic acid having an ethylenically unsaturated group such as 4-methacryloxyethyltrimellitate, an ethylenically unsaturated monomer other than said aromatic dibasic acid and a catalyst is used as a dental adhesive, the composition has a strong adhesiveness to either enamel or dentin of a tooth and the resulting bonded structure is prominently excellent in such properties as water resistance and durability.

It is therefore a primary object of this invention to provide a curable composition which has an excellent adhesiveness to the tooth tissue or a substrate such as a metal and can give a bonded structure excellent in the water resistance and durability.

Another object of the present invention is to provide a curable composition which can be applied to the tooth tissue or a substrate metal without use of a solvent and can be polymerized and cured in situ to form an adhesive layer or undercoat layer.

In accordance with the present invention, there is provided a curable composition comprising (A) an ethylenically unsaturated carboxylic acid represented by the following general formula:

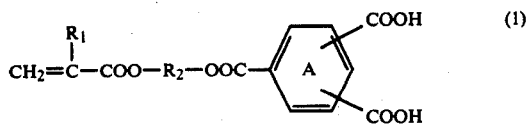

wherein
$R_1$ is a hydrogen atom or a methyl group,
$R_2$ is an alkylene group having 2 to 4 carbon atoms, and in the benzene ring A two carboxyl groups are bonded to carbon atoms other than the carbon atoms adjacent to the carbon atoms to which the ester group is bonded,
or an acid anhydride thereof, (B) at least one ethylenically unsaturated monomer other than said monomer (A), said ethylenically unsaturated monomer (B) being copolymerizable with said monomer (A), and (C) at least one catalyst selected from the group consisting of free radical initiators and photosensitizers.

DETAILED DESCRIPTION OF THE INVENTION

In the ethylenically unsaturated carboxylic acid or its anhydride (A) that is used in the present invention, it is important that two carboxyl groups or one acid anhydride group should be present on the benzene ring, and that in the benzene ring, two carboxyl groups or one acid anhydride group should be bonded to carbon atoms other than the carbon atoms adjacent to the carbon atom to which the ester group is bonded.

A curable composition comprising an ethylenically unsaturated carboxylic acid or its anhydride having the above-mentioned chemical structure has a prominently excellent adhesiveness over a curable composition comprising an ethylenically unsaturated carboxylic acid having one carboxyl group on the benzene ring or an ethylenically unsaturated carboxylic acid having in the benzene ring a carboxyl group bonded to the carbon atom adjacent to the carbon atom to which the ester group is bonded.

An ethylenically unsaturated carboxylic acid or its anhydride most preferred for attaining the objects of the present invention is 4-methacryloxyethyltrimellitate (melting point=119.5° to 120.0° C.) having the following formula:

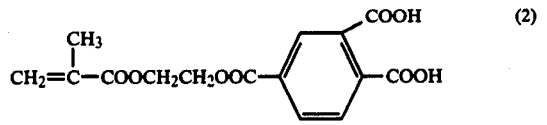

or its anhydride (melting point=95.0° to 95.8° C.) having the following formula:

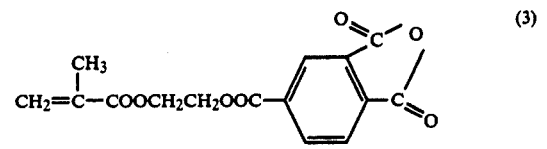

The monomer of the formula (3) may be prepared by dehydrochlorination reaction between hydroxyethyl methacrylate and anhydrous trimellitic acid chloride or by dehydration reaction between hydroxyethyl methacrylate and trimellitic anhydride. 4-Methacryloxyethyltrimmellitate of the formula (2) can easily be prepared by hydration of 4-methacryloxyethyltrimellitate anhydride.

These acid and acid anhydride may be used singly or in the form of a mixture thereof.

As examples of other ethylenically unsaturated carboxylic acids and acid anhydrides that can be used in the present invention, there can be mentioned 4-methacryloxy-3′-propyltrimellitate and its anhydride, 4-acryloxyethyltrimellitate and its anhydride, 4-methacryloxy-4′-butyltrimellitate and its anhydride, and 5-methacryloxyethyltrimesic acid.

As the ethylenically unsaturated monomer (B) that is used in combination with the ethylenically unsaturated carboxylic acid or its anhydride (A) in the present invention, there can be mentioned at least one monomer copolymerizable with said monomer (A). It is preferred that the monomer (B) or at least one of the monomers (B) be liquid in the normal conditions and be capable of dissolving the monomer (A) therein.

As preferred examples of the monomer (B), there can be mentioned acrylic monomers represented by the following general formula:

wherein
$R_1$ is a hydrogen atom or a methyl group
and $R_3$ is an alkyl group having up to 8 carbon atoms, such as methyl acrylate, ethyl acrylate, methyl methacrylate, ethyl methacrylate, butyl methacrylate and 2-ethylhexyl acrylate, and monomers represented by the following general formula:

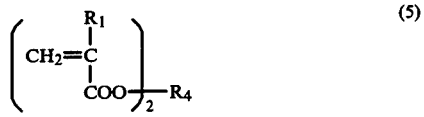

wherein
$R_1$ is a hydrogen atom or a methyl group and
$R_4$ is a divalent organic group.

As the group $R_4$ in the formula (5), there can be mentioned, for example, residues derived from glycols such as ethylene glycol, propylene glycol, tetramethylene glycol, diethylene glycol, triethylene glycol, dipropylene glycol, tripropylene glycol, polyethylene glycol and polypropylene glycol, residues derived from bisepoxy compounds such as 2,2-bis(p-glycidyloxyphenyl)propane, and residues derived from 2,2-bis(p-hydroxyphenyl)propane/ethylene oxide adduct and the like. As specific examples of the monomer represented by the formula (5), there can be mentioned polyethylene glycol dimethacrylate, polypropylene glycol diacrylate and 2,2-bis(p-2'-hydroxy-3'-methacryloxypropoxyphenyl)propane.

In addition, as the monomer (B), there can be used vinyl esters such as vinyl formate, vinyl acetate and vinyl propionate, aromatic vinyl compounds such as styrene, α-methylstyrene, vinyl-toluene and divinylbenzene, ethylenically unsaturated nitriles such as acrylonitrile, methacrylonitrile and α-cyanoacrylic acid esters, vinyl ethers such as butylvinyl ether and octylvinyl ether, vinyl ketones such as ethylvinyl ketone and methylisopropenyl ketone, allyl esters such as diallyl phthalate, and other ethylenically unsaturated carboxylic acids such as itaconic acid and (β-methacryloxy) ethyl maleate.

Among these monomers, an acrylic monomer of the formula (4), especially methyl methacrylate, is preferably used singly or in combination with other monomer.

The content of the above-mentioned ethylenically unsaturated dicarboxylic acid or its acid anhydride (A) can be changed in a broad range according to the intended use of the curable composition of the present invention, namely depending on whether the composition is used as an adhesive or undercoating composition.

In general, however, it is preferred that the amount of the monomer (A) be 0.1 to 20 mole %, especially 1 to 10 mole %, based on the sum of the amounts of the monomers (A) and (B). When the content of the monomer (A) is below the above range, it is often difficult to increase the adhesiveness to a desirable level, and when the content of the monomer (A) is above the above range, no particular improvement of the adhesiveness can be expected and the use of such a large amount of the monomer (A) is not preferred from the economical viewpoint.

In the present invention, a free radical initiator or photosensitizer is incorporated in a mixture of the monomers (A) and (B) as the catalyst (C).

As the free radical initiator, peroxides and peracids such as benzoyl peroxide, dicumyl peroxide, cumene hydroperoxide and t-butyl perbenzoate and azo compounds such as azobisisobutyronitrile are ordinarily used, if desired, in combination with polymerization promoters such as organic acid amides and organic acid imides. When the curing is conducted at room temperature, it is preferred to use partially oxidized tri-n-butylborane or a mixture of cobalt naphthenate and methylethyl ketone peroxide.

Any of known photosensitizers can be used in the present invention. For example, there can be used benzoin methyl ether, benzoin ethyl ether, benzoin isopropyl ether, acetophenone, benzophenone and anthraquinone.

The catalyst is used in a so-called catalytic amount, namely 0.01 to 10% by weight, especially 0.1 to 5% by weight, based on the sum of the amounts of the monomers (A) and (B).

The curable composition of the present invention may further comprise various additives. As additives that can be used in the present invention, there can be mentioned inorganic powdery fillers such as kaolin, talc, clay, calcium carbonate, silica, alumina, silica-alumina, calcium phosphate and glass, pigments such as titanium oxide, tackifying agents such as waxes and ethylene/vinyl acetate copolymers, curing promotors, polymerization regulators and polymerization inhibitors such as hydroquinone.

The curing composition of the present invention is used as an adhesive, an undercoating agent or the like in the form of a homogeneous liquid formed by homogeneously dissolving the ethylenically unsaturated carboxylic acid or its anhydride (A) into the liquid ethylenically unsaturated monomer (B) and adding the catalyst (C) to the resulting solution.

The curable composition of the present invention can be cured to form a cured resin layer when it is allowed to stand at room temperature or it is heated if necessary. When a photosensitizer is incorporated as the catalyst (C), the composition of the present invention is cured under irradiation of ultraviolet rays to form a cured resin layer.

When a powder of an acrylic or methacrylic resin, for example, a polymethyl methacrylate powder, is present in the curable composition at the curing step, a cured resin layer is formed in a relatively short time. Accordingly, this feature is preferred when the composition of the present invention is used as an adhesive. It is preferred that such resin powder be made present in an amount of 0.1 to 2 parts by weight per part by by weight of the sum of the monomers (A) and (B).

According to a preferred embodiment of the application of the curable composition of the present invention, 4-methacryloxyethyltrimellitate anhydride (A) is mixed with partially oxidized tri-n-butylborane (C) and methyl methacrylate (B) at room temperature to form a cured resin. Further, 4-methacryloxyethyltrimellitate anhydride (A) is mixed with a small amount of benzoin methyl ether (C) and methyl methacrylate (B) and the mixture is irradiated with ultraviolet rays, whereby a cured resin can easily be formed.

When the curable composition of the present invention is used as an adhesive, the composition is applied to at least one of the surfaces of articles to be bonded, for example, teeth, metals and resins, then the articles are bonded together before the composition is cured thoroughly, so it can be obtained a high adhesive strength.

The curable composition of the present invention can be used especially valuable as dental materials, for example, a pit and fissure sealant, an orthodontic adhesive, a filling composite resin, a resin for veneered crown, a metallic denture base resin or an adhesive for bonding a metal or the like to teeth.

When the curable composition of the present invention is used as an undercoating composition for an adhesive or paint, the composition of the present invention is applied to a substrate and cured, and a known adhesive is applied to the resulting cured resin layer and bonding is effected or a paint is applied to the cured resin layer to form a coated structure. When the composition of the present invention is used as an undercoating composition, the adhesion or bonding strength can be remarkably improved over the adhesion or bonding strength attained when the composition of the present invention is not used.

The curable composition of the present invention can be applied to usage as an adhesive, an undercoating composition and the like in the form of a single composition formed by preliminarily mixing the three ingredients. Further, the respective ingredients are applied to the surface of a substrate to be bonded or coated to form the composition of the present invention thereon and the composition is thus applied to the above-mentioned uses.

For example, there may be adopted a method in which 4-methacryloxyethyltrimellitate or its anhydride (A) is dissolved in a solvent such as a ketone or an alcohol, the resulting solution is coated on a substrate, the solvent is evaporated from the coating, and an ethylenically unsaturated compound (B) with a free radical initiator and/or a photosensitizer (C) is applied to the coating to effect curing and form a cured resin layer.

Since the above-mentioned specific ethylenically unsaturated dicarboxylic acid or its anhydride is contained in the curable composition of the present invention, the composition has a very high adhesiveness or bonding strength to the surfaces of various substrates, especially the surface of enamel or dentin of a tooth or the surface of a metal, and provides a bonding especially excellent in the water resistance and durability.

As the tooth adhesive, there has been known a methyl methacrylate polymer or a copolymer of methyl methacrylate with a vinyl compound such as 2,2-bis(p-2'-hydroxy-3'-methacryloxypropoxyphenyl)propane. However, since these known adhesives are still insufficient in the bondability to teeth, they are applied to teeth after the teeth have been treated with strong acids. In contrast, the curable composition of the present invention containing an ethylenically unsaturated carboxylic acid such as 4-methacryloxyethyltrimellitate or its anhydride has a sufficiently high bondability to teeth. Accordingly, the acid treatment indispensable in the conventional techniques need not be conducted, and therefore, the dental treatment can be remarkably facilitated and the loss of the surface portion of a tooth by the acid treatment can be completely prevented. Therefore, the present invention makes great contributions to the art.

The present invention will now be described in detail by reference to the following Examples that by no means limit the scope of the invention.

EXAMPLE 1

The flat labial enamel surface of fresh borine upper incisal tooth was obtained by polishing with emery papers (up to No. 6/0). A cellophane tape having a size of 13 mm × 13 mm with a circular hole of a diameter of 5.4 mm in the center was fixed to the enamel surface. A 5% acetone solution of 4-methacryloxyethyltrimellitate anhydride was coated to the hole two times by using a small brush. Then, a mixture of a methyl methacrylate monomer containing 4% of partially oxidized tri-n-butylborane as a polymerization initiator and powdery polymethyl methacrylate in an amount of 20% based on monomer was coated by using another small brush. Next a polymethylmethacrylate rod having a diameter of 5 mm was placed on the curing mass at room temperature. After one hour had passed, the bonded sample was dipped in water maintained at 37° C. for 24 hours. The sample was taken out from water and polymethylmethacrylate rod was pulled from the borine enamel at a loading speed of 2 mm/min by using a Universal Testing Machine Model IM-500 (Shimazu Seisakusho Kyoto, Japan). It was found that the tensile adhesive strength was 34.6 Kg/cm$^2$.

COMPARATIVE EXAMPLE 1

The procedures of Example 1 were repeated in the same manner except that coating with the 5% acetone solution of 4-methacryloxyethyltrimellitate anhydride was omitted. The tensile adhesive strength was 0 Kg/cm$^2$.

COMPARATIVE EXAMPLE 2

The procedures of Example 1 were repeated in the same manner except that a 5% acetone solution of methacryloxyethyl phthalate was used instead of the 5% acetone solution of 4-methacryloxyethyltrimellitate anhydride. The tensile adhesive strength was 9.1 Kg/cm$^2$.

COMPARATIVE EXAMPLE 3

The procedures of Example 1 were repeated in the same manner except that a 5% acetone solution of N-acryloyl-$\gamma$-aminosalicylic acid was used instead of the 5% acetone solution of 4-methacryloxyethyltrimellitate anhydride. The tensile adhesive strength was 6.3 Kg/cm$^2$

COMPARATIVE EXAMPLE 4

The procedures of Example 1 were repeated in the same manner except that a 5% acetone solution of N-methacryloylaspargic anhydride was used instead of the 5% acetone solution of 4-methacryloxyethyltrimellitate. The tensile adhesive strength was 2.7 Kg/cm$^2$.

EXAMPLE 2

A flat labial enamel surface of fresh borine upper incisal tooth was obtained by polishing with emery papers up to (No. 6/0). A cellophane tape having size of 13 mm × 13 mm with a circular hole of a diameter of 5.4 mm in the center was fixed to the enamel surface. Then, a mixture of monomer solution made from 95% by weight of methyl methacrylate and 5% 4-methacryloxyethyltrimellitate anhydride, partially oxidized tri-n-butylborane as a polymerization initiator in an amount of 4% based on monomer solution and powdery polymethyl methacrylate in an amount of 20% based on monomer solution was coated by using a small brush. Next a polymethylmethacrylate rod having a diameter of 5 mm was placed on the curing mass at room temperature. After one hour had passed, the bonded sample was dipped in water maintained at 37° C. for 24 hours. The sample was taken out from water and the polymethylmethacrylate rod was pulled from the borine enamel at a loading speed of 2 mm/min by using a Universal Test Machine Model IM-500. It was found that the tensile adhesive strength was 56.8 Kg/cm$^2$.

COMPARATIVE EXAMPLES 5 TO 7

The procedures of Example 2 were repeated in the same manner except that a monomer or mixture indicated in Table 1 was used instead of the mixture of 95% by weight of methyl methacrylate and 5% by weight of 4-methacryloxyethyltrimellitate anhydride. In each run, the tensile adhesive strength was 0 Kg/cm$^2$.

Table 1

| | Composition (% by weight) of monomers in Adhesive | Tensile Adhesive Strength (Kg/cm$^2$) |
|---|---|---|
| Example 2 | 4-methacryloxyethyltrimellitate anhydride, 5 methyl methacrylate, 95 | 56.8 |
| Comparative Example 5 | methyl methacrylate, 100 | 0 |
| Comparative Example 6 | Bis-GMA*, 5 methyl methacrylate, 95 | 0 |
| Comparative Example 7 | HNPM**, 5 methyl methacrylate, 95 | 0 |

Note
*2,2-bis(p-2'-hydroxy-3'-methacryloxypropoxyphenyl)propane
**2-hydroxy-3-β-naphthoxypropyl methacrylate

EXAMPLE 3

The procedures of Example 1 were repeated in the same manner except that a 5% acetone solution of 4-methacryloxyethyltrimellitate was used instead of the 5% acetone solution of 4-methacryloxyethyltrimellitate anhydride. The tensile adhesive strength was 30.8 Kg/cm$^2$.

EXAMPLE 4

The procedures of Example 2 were repeated in the same manner except that a mixture of 95% by weight of methyl methacrylate and 5% by weight of 4-methacryloxyethyltrimellitate was used instead of the mixture of 95% by weight of methyl methacrylate and 5% by weight of 4-methacryloxyethyltrimellitate anhydride. The tensile adhesive strength was 40.6 Kg/cm$^2$.

EXAMPLE 5

When the tensile adhesive strength was determined according to the method described in Example 1, a 2/1 weight ratio mixture of Bis-GMA/triethylene glycol dimethacrylate was used as the ethylenically unsaturated monomer (B) and 0.5% by weight of benzoin methyl ether was incorporated and sufficiently dissolved in the mixture. The so formed viscous liquid was thinly coated on the surface of a bovine tooth exposed through a circular hole formed on a cellophane tape in the same manner as described in Example 1. Then, ultraviolet rays were applied to the coated surface for 1 minute by using an ultraviolet ray irradiator (Nuva Lite manufactured by L. D. Calk Co.) to effect curing. Then, an acrylic resin rod was bonded to the cured resin layer by using a methyl methacrylate type adhesive. The rod-bonded bovine tooth was dipped in water maintained at 37° C. for 24 hours, and the tensile adhesive strength was measured in the same manner as described in Example 1. It was found that the tensile adhesive strength was 45.8 Kg/cm$^2$.

COMPARATIVE EXAMPLE 8

The procedures of Example 5 were repeated in the same manner except that coating with the 5% acetone solution of 4-methacryloxyethyltrimellitate anhydride was omitted. The tensile adhesive strength was 3.2 Kg/cm$^2$.

EXAMPLE 6

A cubic having a size of 1 cm × 1 cm × 1 cm was cut from wetted ivory, and in the same manner as described in Example 2, an acrylic resin rod was bonded to one surface of this ivory cubic. The acrylic resin rod-bonded ivory cubic was dipped in water maintained at 37° C. for 7 days. Then, the ivory cubic was dipped in water maintained at 4° C. for 1 minute and in hot water maintained at 60° C. for 1 minute, and this alternate dipping was repeated 800 times. The acrylic resin rod was not pulled from the ivory cubic even if a pulling force of 40 Kg/cm$^2$ was applied.

COMPARATIVE EXAMPLE 9

The procedures of Example 6 were repeated in the same manner except that methyl methacrylate was used instead of the mixture of 95% by weight of methyl methacrylate and 5% by weight of 4-methacryloxyethyltrimellitate anhydride. The alternating dipping in water maintained at 4° C. for 1 minute and in hot water maintained at 60° C. for 1 minute was repeated 300 times. The acrylic resin rod was pulled off from the ivory cubic when a pulling force of 8 Kg/cm$^2$ was applied.

EXAMPLE 7 AND COMPARATIVE EXAMPLE 10

The flat surface of a metal piece having a size of 1 cm × 1 cm was sufficiently ground by an emery paper No. 1 to attain a certain smoothness on the surface. A cellophane tape having a size of 1 cm × 1 cm and a circular hole having a diameter of 5.4 mm was applied to the ground surface of the metal piece. Partially oxidized tri-n-butylbornae was incorporated as the free radical initiator in an amount of 8% by weight into a monomer mixture comprising 95% by weight of methyl methacrylate and 5% by weight of 4-methacryloxyethyltrimellitate anhydride, and a small amount of powdery polymethyl methacrylate was added to the mixture to form an adhesive composition. The composition was coated on the metal piece surface exposed through the circular hole of the cellophane tape and an acrylic resin rod having a diameter of 5 mm was vertically held and fixed on the coated surface of the metal piece. After one hour had passed, the cellophane tape was peeled off, and the acrylic resin rod-bonded metal piece was dipped in water maintained at 37° C. for a predetermined time. Then, the metal piece was taken out from water and the acrylic resin rod was pulled from the metal piece at a loading speed of 2 mm/min by using universal testing machine (Model IM-500) to determine the tensile adhesive strength.

For comparison, the above procedures were repeated in the same manner except that 4-methacryloxyethyltrimellitate anhydride was not used but methyl methacrylate alone was used. The tensile adhesive strength was determined in the same manner as described above.

Obtained results are shown in Table 2.

Table 2

| Metal Piece | Dipping Time (days) | Tensile Adhesive Strength (Kg/cm$^2$) |
|---|---|---|
| Example 7 | | |
| Suncolium | 2 | above 145.9* |
| " | 30 | above 185.6* |
| Sunilium | 6 | above 103.1* |
| Brass | 4 | 121.4 |
| Gold-silver-palladium | 30 | 76.9 |
| Silver alloy | 1 | above 190.0* |
| Comparative Example 10 | | |
| Suncolium | 2 | 22.8 |
| Sunilium | 6 | 67.7 |

Note
Suncolium: cobalt-chromium alloy for dental casting (manufactured by Sankin Kogyo)
Sunilium: nickel-chromium alloy for dental casting (manufactured by Sankin Kogyo)
Gold-silver-palladium: 12 % of gold, 20 % of palladium, 57.8 % of silver and 9.9 % of copper
Silver alloy: 60 % of silver, 25 % of tin, 10 % of copper and 1 % of palladium
*the adhesive layer of the acrylic resin rod was destroyed at the measurement of the tensile adhesive strength

EXAMPLE 8 AND COMPARATIVE EXAMPLE 11

An acrylic resin rod was bonded to a copper piece according to the procedures of Example 7. The copper piece was dipped in water maintained at 37° C. for 1 day, and it was then dipped in water maintained at 4° C. for 1 minute and in water maintained at 60° C. for 1 minute alternately. This alternate dipping was conducted 60 times, namely for 2 hours as a whole. At the measurement of the tensile adhesive strength, the acrylic resin rod was destroyed when a pulling force of 149.3 Kg/cm$^2$ was applied.

For comparison, the above procedures were repeated in the same manner except that 4-methacryloxyethyltrimellitate anhydride was not used but methyl methacrylate alone was used. The tensile adhesive strength was 37.6 Kg/cm$^2$.

EXAMPLE 9 AND COMPARATIVE EXAMPLE 12

In the same manner as described in Example 8 or Comparative Example 11, a stainless steel piece (SUS 304) and an acrylic resin rod were bonded together. It was found that the tensile adhesive strength was 105 Kg/cm$^2$ when 4-methacryloxyethyltrimellitate anhydride was used in combination with methyl methacrylate (Example 9) and the tensile adhesive strength was 10 Kg/cm$^2$ when methyl methacrylate alone was used (Comparative Example 12).

EXAMPLE 10

A liquid mixture comprising 63 parts by weight of Bis-GMA, 32 parts by weight of triethylene glycol dimethacrylate and 5 parts by weight of 4-methacryloxyethyltrimellitate anhydride was prepared, and 0.5% by weight of benzoin peroxide was added to the liquid mixture to form a homogeneous solution. The viscous liquid was coated on the surface of a stainless steel sheet (SUS 304) having a thickness of 1 mm, a width of 10 mm and a length of 100 mm, and the coated surface was lightly covered with a cellophane paper. The coated steel sheet was maintained in a thermostat tank maintained at 70° C. for 3 hours to form an adhesive layer. The, a methylene chloride solution of polymethyl methacrylate containing a small amount of a dye (Oil Red) was coated on the adhesive layer. Methylene chloride was evaporated to form a colored layer. The so treated SUS 304 sheet was dipped in water maintained at 50° C. for 1 month. The sheet was taken out from water and water was wiped away from the sheet. Then, an adhesive cellophane tape was applied to the colored layer, and the cellophane tape was violently peeled off while the SUS sheet was being firmly fixed. The colored layer was not peeled off but was held on the SUS sheet.

COMPARATIVE EXAMPLE 13

The procedures of Example 10 were repeated in the same manner except that formation of the adhesive layer was omitted. The colored layer-bonded SUS sheet was dipped in water maintained at 50° C. only for one day. When the cellophane tape was peeled from the SUS sheet, the colored layer was readily peeled off from the SUS sheet together with the cellophane tape.

What we claim is:

1. A curable composition comprising (A) an ethylenically unsaturated carboxylic acid represented by the following general formula:

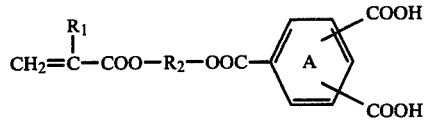

wherein
R$_1$ is a hydrogen atom or a methyl group,
R$_2$ is an alkylene group having 2 to 4 carbon atoms, and in the benzene ring A, two carboxyl groups are bonded to carbon atoms other than the carbon atoms adjacent to the carbon atom to which the ester group is bonded,
or an acid anhydride thereof, (B) at least one ethylenically unsaturated monomer other than said monomer (A), said ethylenically unsaturated monomer (B) being copolymerizable with said monomer (A), and (C) at least one catalyst selected from the group consisting of free radical initiators and photosensitizers.

2. A curable composition as set forth in claim 1 wherein the ethylenically unsaturated carboxylic acid is 4-methacryloxyethyltrimellitate.

3. A curable composition as set forth in claim 1 wherein the acid anhydride is 4-methacryloxyethyltrimellitate anhydride.

4. A curable composition as set forth in claim 1 wherein the ethylenically unsaturated monomer (B) is an acrylic monomer represented by the following general formula:

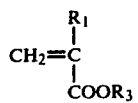

wherein
$R_1$ is a hydrogen atom or a methyl group, and
$R_3$ is an alkyl having up to 8 carbon atoms.

5. A curable composition as set forth in claim 1 wherein the ethylenically unsaturated monomer (B) is a monomer represented by the following general formula:

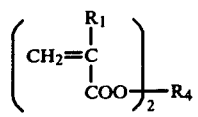

wherein
$R_1$ is a hydrogen atom or a methyl group and
$R_4$ is a divalent organic group.

6. A curable composition as set forth in claim 1 wherein the ethylenically unsaturated monomer (B) is an aromatic vinyl monomer.

7. A curable composition as set forth in claim 1 wherein the ethylenically unsaturated carboxylic acid or its acid anhydride (A) is present in an amount of 0.1 to 20 mole % based on the sum of the amounts of said monomers (A) and (B).

8. A curable composition as set forth in claim 1 wherein the catalyst (C) is present in an amount of 0.1 to 5% by weight based on the sum of the amounts of said monomers (A) and (B).

9. A curable composition as set forth in claim 1 which further comprises a powder of an acrylic or methacrylic resin.

10. A curable composition as set forth in claim 9 wherein the powder of the acrylic or methacrylic resin is present in an amount of 0.1 to 2 parts by weight per part by weight of the sum of the amounts of said monomers (A) and (B).

11. A dental adhesive comprising a curable composition as set forth in claim 1.

* * * * *